(12) United States Patent
Diller et al.

(10) Patent No.: US 7,868,144 B2
(45) Date of Patent: Jan. 11, 2011

(54) METHOD FOR UNSPECIFIC ENRICHMENT OF BACTERIAL CELLS

(75) Inventors: Sabine Diller, Schwandorf (DE); Renate Grassl, Regensburg (DE); Stefan Miller, Regensburg (DE); Ingrid Robl, Regensburg (DE); Michael Schütz, Lappersdorf (DE); Thomas Zander, Lappersdorf (DE)

(73) Assignee: Hyglos Invest GmbH, Bernried (DE)

( * ) Notice: Subject to any disclaimer, the term of this patent is extended or adjusted under 35 U.S.C. 154(b) by 0 days.

(21) Appl. No.: 10/492,230

(22) PCT Filed: Oct. 8, 2002

(86) PCT No.: PCT/DE02/03790

§ 371 (c)(1),
(2), (4) Date: Sep. 16, 2004

(87) PCT Pub. No.: WO03/033698

PCT Pub. Date: Apr. 24, 2003

(65) Prior Publication Data

US 2005/0019827 A1    Jan. 27, 2005

(30) Foreign Application Priority Data

Oct. 9, 2001 (DE) ................................ 101 49 803
Jul. 4, 2002 (DE) ................................ 102 30 147

(51) Int. Cl.
*A23J 1/00* (2006.01)
*G01N 33/00* (2006.01)
*G01N 33/53* (2006.01)
*G01N 33/567* (2006.01)

(52) U.S. Cl. .................... 530/412; 435/7.25; 435/7.2; 435/7.21; 435/7.9

(58) Field of Classification Search ................ 530/412; 435/383, 7.25, 7.2, 7.21, 7.9
See application file for complete search history.

(56) References Cited

U.S. PATENT DOCUMENTS

| 4,647,536 | A |   | 3/1987 | Mosbach et al. | ............ 435/177 |
|---|---|---|---|---|---|
| 5,051,189 | A |   | 9/1991 | Farrah | ............ 210/679 |
| 5,075,430 | A |   | 12/1991 | Little | ............ 536/27 |
| 5,208,166 | A |   | 5/1993 | Saunders et al. | ............ 436/518 |
| 5,464,541 | A |   | 11/1995 | Aysta et al. | ............ 210/767 |
| 5,489,401 | A |   | 2/1996 | Freeman | ............ 264/4.3 |
| 5,536,644 | A | * | 7/1996 | Ullman et al. | ............ 435/7.25 |
| 5,770,388 | A | * | 6/1998 | Vorpahl | ............ 435/7.25 |
| 6,020,186 | A |   | 2/2000 | Henco et al. | ............ 435/287.2 |
| 6,284,470 | B1 |  | 9/2001 | Bitner et al. | ............ 435/6 |
| 6,548,523 | B2 |  | 4/2003 | Lawrence et al. | ............ 514/357 |

FOREIGN PATENT DOCUMENTS

| EP | 1118676 | 7/2001 |
|---|---|---|
| WO | WO 98/51693 | 11/1998 |
| WO | WO 01/46266 | 6/2001 |
| WO | WO 01/51206 | 7/2001 |
| WO | WO 01/53525 | 7/2001 |

OTHER PUBLICATIONS

Robert B. White, Determination of magnetic susceptibility for magnetotatic bacteria, pp. 1-24, http://shiro.wustl.edu/research/magsus/isef96_paper.htm, Aug. 2005.*

Frankel et al, Magnetotaxis in Bacteria, 2001, pp. 1-9, http://www.calpoly.edu/~rfrankel/magbac101.html.*

* cited by examiner

*Primary Examiner*—Vanessa L Ford
*Assistant Examiner*—Lakia J Tongue
(74) *Attorney, Agent, or Firm*—Fulbright & Jaworski

(57) ABSTRACT

The present invention relates to a method for unspecific enrichment of bacterial cells by means of cationic or anionic polymers and magnetic carriers.

13 Claims, 10 Drawing Sheets

METHOD FOR UNSPECIFIC ENRICHMENT OF BACTERIAL CELLS

Figure 1:
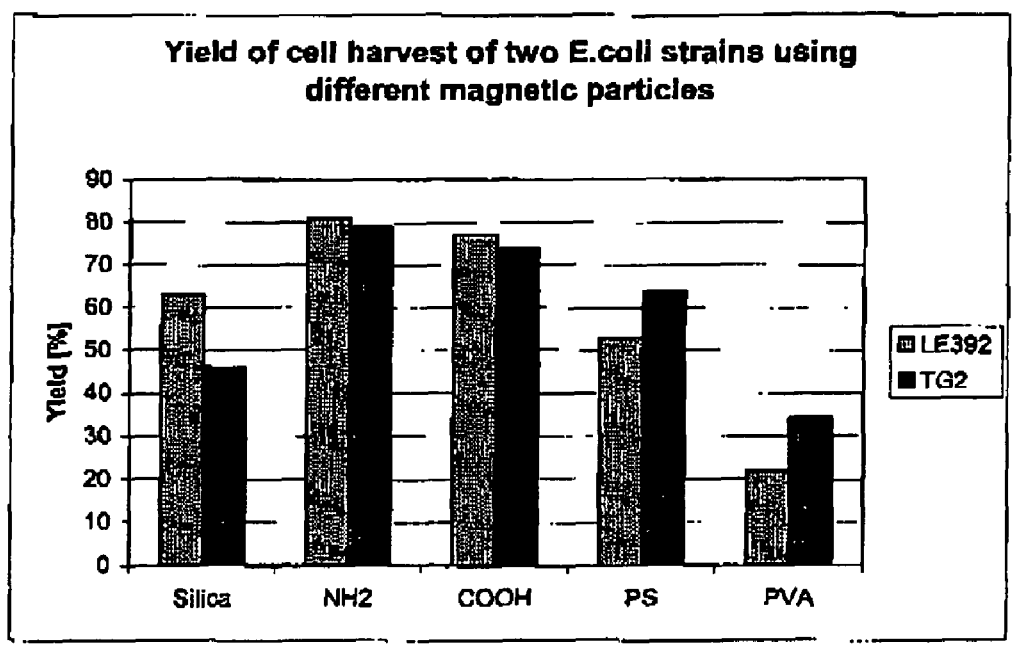

This application claims priority to PCT/DE 02/03790, filed on Oct. 8, 2002. The entire content of this application is incorporated by reference.

The present invention relates to a method for unspecific enrichment of bacterial cells by means of cationic or anionic polymers and magnetic carriers.

Starting point of almost every processing, analysis or isolation of components of cells is the enrichment of the cells, the "cell harvest". The letter is usually performed by centrifugation. This centrifugation step poses the main problem within the full automation of methods, like the purification of plasmids, because an extremely high precision is necessary at the start and the stop position of the process of centrifugation, besides the high technical effort for the integration of a centrifuge into a corresponding robot. Automatic methods in processing, analysis or isolation of compounds of cells, therefore usually start with cells, which have been enriched, centrifuged or sedimented already outside of the robot. However, a possibly full automation of the therefore relevant methods is essential, e.g. for a quick analysis of entire genomes, proteomes but also for the rapid resolving of structures and functions in high-through-put methods. Nevertheless the automation of partial steps, e.g. in the genome analysis, is already very advanced: Both the cultivation of bacteria and the isolation of plasmids can be performed automatically. However a simple, inexpensive and complete automation of the method, including the cell harvest, is not feasible by now.

The standard method of the cell harvest is the centrifugation of the bacterial cultures. For this a micro-titre-plate centrifuge is necessary, especially in the methods that are to be designed for a higher throughput.

An alternative method makes use of the enrichment of cultivated cells by filter-membranes (e.g. WO 01/51206, 3 M Innovative Properties Co (US) and U.S. Pat. No. 5,464,541, Diagen Institut f. Molekularbiologie). However this method appears to be very accident sensitive in respect of plugging in the case of the use of highly enriched cell suspensions and as a consequence thereof the high viscosity of the solutions. Similarly this holds true for the ion exchanger-like binding to a porous matrix, combined with filtration- and vacuum-techniques (WO 92/07863, Qiagen). This may pose major problems especially for automatic methods.

An enrichment of micro-organisms by means of methods that are based on magnetic particles are in principal suited for automation. By now three methods for the enrichment of bacteria have been described, but which show clear disadvantages in the aspect of strain specificity and the expenses for their production.

EP 1 118676 A2, Chemagen AG and WO 01/53525 A2, Genpoint AS describe a method for the enrichment of micro-organisms at a solid phase by a non-specific ligand, which is immobilised at this solid phase covalently or non-covalently. Solid phases, in terms of this method, are polyvinylalkohol-beads, which may be magnetic or non-magnetic. In the sense of this method molecules are regarded as ligands, which can serve as nutrients for the micro-organisms. The disadvantage of this method resides in the fact that certain ligands have to be immobilised on a support, which leads to a significant increase of the expenses of their production. A further disadvantage resides in the fact that possibly different ligands have to be immobilised for different strains which means that the magnetic beads and therefore the method are not all-purpose.

In a further application, namely WO 98/51693, Genpoint, mixtures of salts, alcohols and polyethylene glycol or polymers that can be compared to polyethylene glycol are described for the enrichment of bacteria on magnetic particles. The method described in WO 98/51693 takes 5-20 minutes and the addition of polymers of 2-50% (w/v). These high concentrations of salts or polymers pose problems in the further processing of the bacteria because e.g. polyethylene glycol is very pasty at 30% or high concentrations of salt interfere with the SDS polyacrylamide gel electrophoresis.

WO 00/29562, Merck Patent GmbH, describe a method for the isolation of plasmid-DNA from micro-organisms by a) acidifying the culture of micro-organisms, incubation and mixture with the solid face materials (silica-magnetic-particles) and b) a subsequent purification of the plasmids. However this method is not feasible for all E. coli-strains without to some extent drastic losses in the rate of yield. A further disadvantage of this method resides in the amount of beads needed because the expenses for the beads make up the main focus of the expenses of the enrichment of the bacteria and especially the silica-beads are relatively expensive. Since silica-beads can bind principally to DNA also losses in the rate of yield during the isolation of the plasmids with silica-beads can be observed, too.

WO 91/12079, Amersham, describes a method for the precipitation of cells at magnetic-beads that bind unspecifically to the polymers (cells). In this method the order of the addition of the necessary agents (alcohol and salt) and of the magnetic beads is to be obeyed compulsory. A mixing of the agents and/or agents and beads prior to use is not possible and therefore no pipetting steps can be spared, what might be necessary in an automation for the optimal exploitation of a robot. Furthermore the magnetic particles that can be used are restricted to cellulose/ferrous oxide-particles.

U.S. Pat. No. 6,284,470 B1, Promega, describes the complexation of intact cells with magnetic particles. In terms of the applicable magnetic bead this method is restricted to silica-particles. Since this method prescribes that one volume of alcohol has to be added to one volume of cell suspension this method appears hardly applicable for the cell harvest in deep-well-plates without any significant losses in the rate of yield. Furthermore high concentrations of alcohol can lead to a precipitation of proteins.

A number of studies showed that cationic polymers can interact with bacteria. Experiments e.g. showed that cationic polymers like e.g. chitosan (chitosan is deacetylated chitin) are well suited for the encapsulation or "sealing" of living microbial cells for single cell experiments (see e.g. Methods Enzymol. 1987, vol. 135, 259-268, or U.S. Pat. No. 5,489, 401). Chitosan is also used for the encapsulation of active biomaterials in bead-polymeres (U.S. Pat. No. 4,647,536 and WO 01/46266). Chitosan is also used—optionally also in modified form—for coating of articles or experimental kits for immunoassays (U.S. Pat. No. 5,208,166).

However publications concerning the influence of cationic polymers on the hydrophobicity of microbial cell-walls have shown that the adhesion to hydrophobic surfaces at pH-values above 3 significantly increased but decreased to almost 0% at pH-values less than 3 (Ref.: Goldberg, S., Doyle, R. J. and Rosenberg, M., 1990, J. Bacteriol. vol. 172, 5650-5654).

The use of a method, which is supported by magnetic particles moreover offers further advantages because a separate harvest of single wells, e.g. in a deep-well-plate, becomes possible and the entire plate has not to be harvested completely. Therefore, e.g. within the scope of expression studies, the harvest can take place in a time dependent manner.

In summary it can be assessed that at present there is no simple method for an efficient, fast, inexpensive enrichment of bacterial cells which gets along without a centrifugation step and which in the same time can be used for a broad variety of bacteria. Therefore it is the task of the present invention to provide a method for the unspecific enrichment of bacterial cells that gets along without a centrifugation step.

This problem is solved by the subject-matter which is defined by the patent claims.

The invention is illustrated by the following figures in more detail:

FIG. 1 graphically shows the result of the yield of the cell harvest of *E. coli* LE392 (bright bars) and TG2 (dark bars) using different magnetic particles. The values indicate the yield in % determined by the ratio of the turbidity of the supernatant and the optical density of the used cell suspension. The abbreviations represent: Silica: MagPrep™ Silica Beads (magnetic, silica coated iron particles, Fa. MERCK, Darmstadt, Germany), $NH_2$: amino-polystyrene-beads (Fa. Estapor, MERCK-Eurolab); COOH: carboxy-polystyrene-beads (Fa. Estapor, MERCK-Eurolab); PS: polystyrene-beads (Spherotech, Illinois, USA); PVA: polyvinylalcohol-beads (Chemagen, Baesweiler, Germany).

Figure 2:
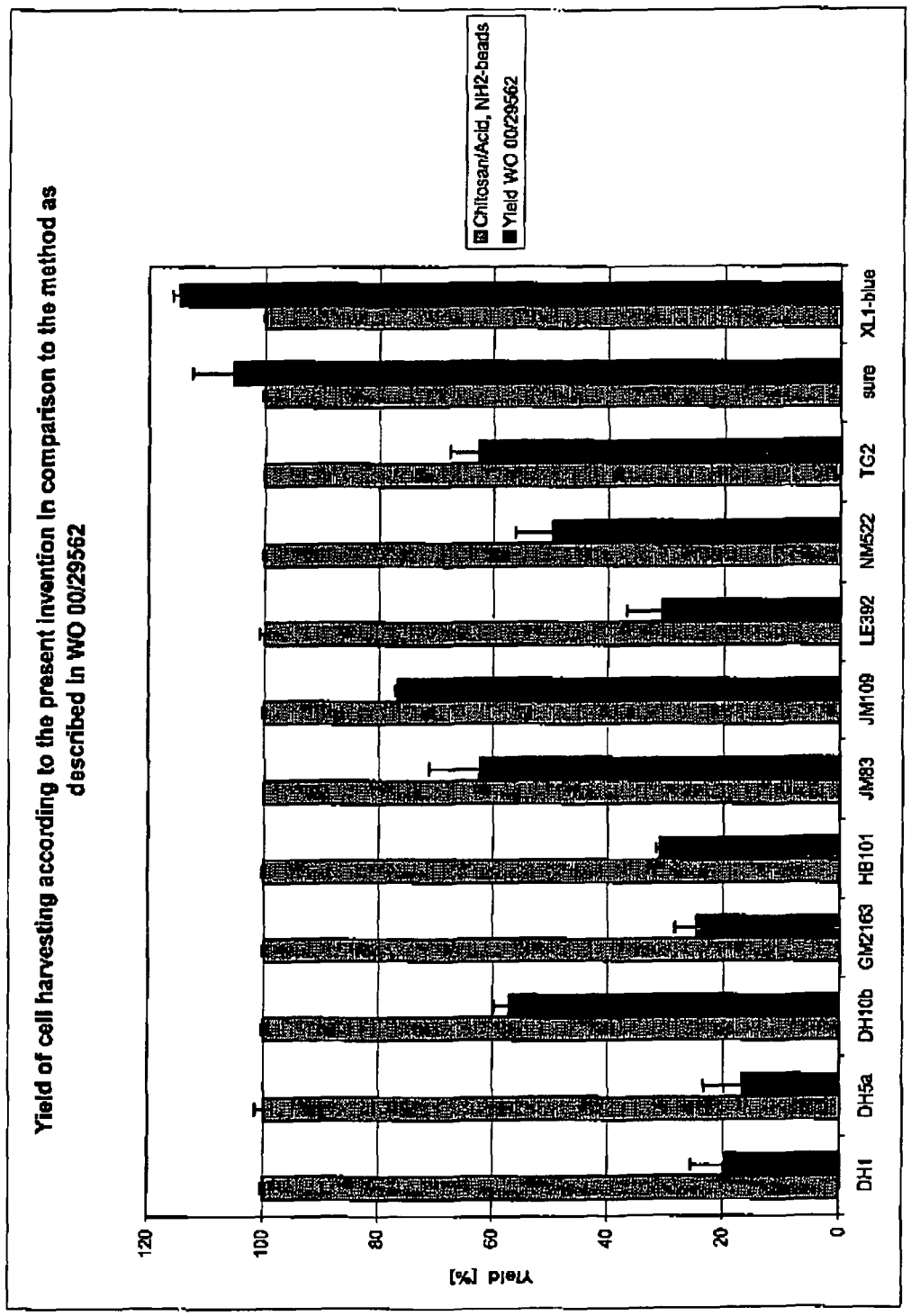

FIG. 2 shows the result of the yield of the cell harvest at an acidic pH-value with silica-beads (dark bars) and chitosan/amino-polystyrene-beads (bright bars). In FIG. 2 the yield of the cell harvest of the method according to the present invention (bright bar) is compared with the method from WO 00/29562 (dark bar). The yields of the cells of the method according to the present invention are set to 100%, the yields according to WO 00/29562 were determined in relation to this. All values are mean values from several experiments with standard deviations. The cell harvest of the method according to the present invention was performed as described in the example 5. For WO 00/29562/MERCK the protocol of the manufacturer was followed.

Figure 3:
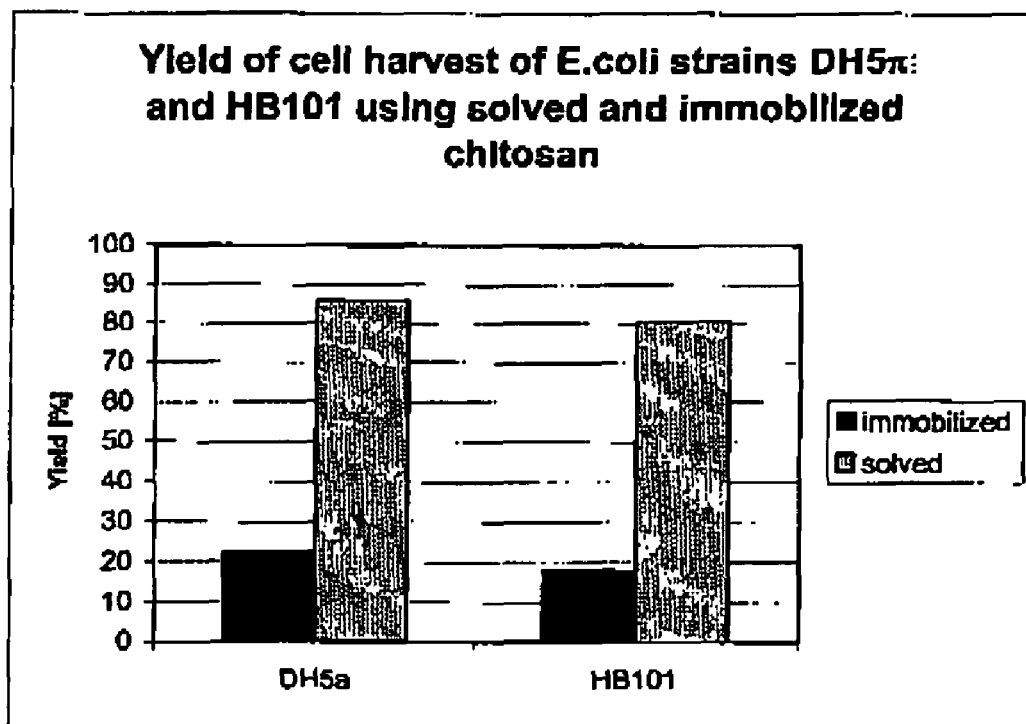

FIG. 3 graphically displays the result of the yield of the cell harvest for *E. coli* strains DH5α and HB101 using solved chitosan (bright bars) and chitosan which was immobilised at beads (Chitosan-beads, Fa. Chemicell, Berlin, Germany) (dark bars). The values indicate the yield in % determined from the ratio of the optical density of the supernatant and the used cell suspension.

Figure 4:
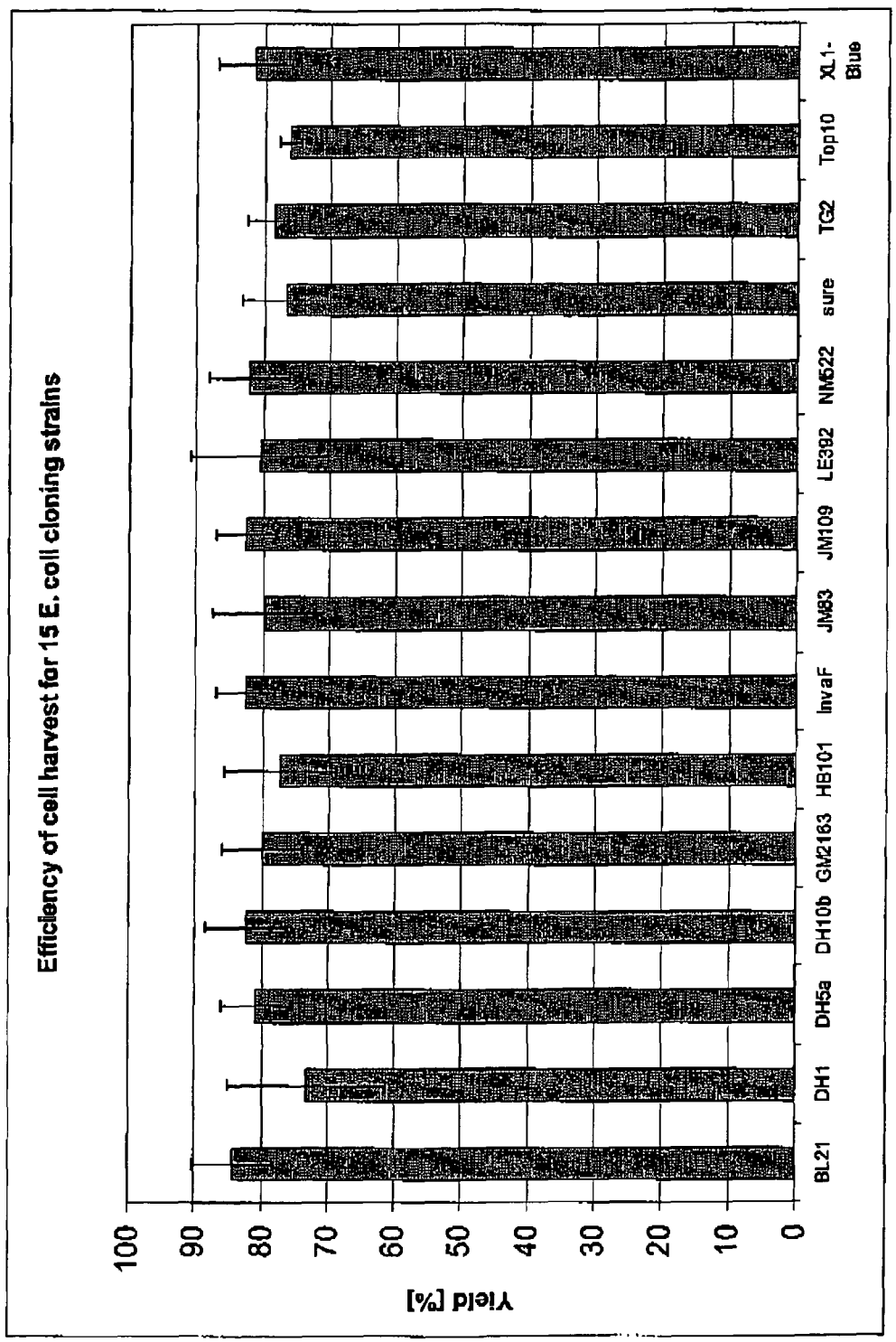

FIG. 4 shows a graphic view depicting the result of the efficiency of the yield of the cell harvest (performed like in example 5) by means of an assortment of 15 *E. coli* cloning strains. The yield is plotted in % (mean values from several experiments, n=27), determined from the ratio of the optical density of the supernatant and the used cell suspension.

Figure 5:
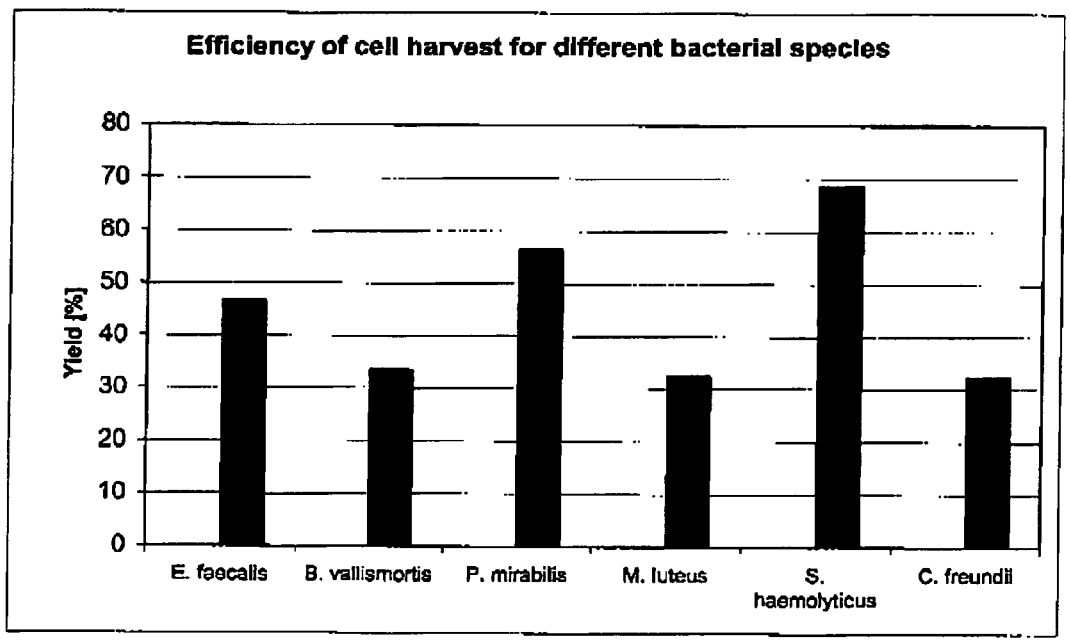

FIG. 5 shows the result of the harvest of different bacterial species. FIG. 5 shows that the system for the cell harvest according to the present invention can be used for a broad spectrum of bacteria of several groups (both gram-negative and gram-positive bacteria). In each case the yield of the cell harvest is plotted. The cells were harvested like depicted in Example 7. *E. faecalis: Enterococcus faecalis, B. vallismortis: Bacillus vallismortis, P. mirabilis: Proteus mirabilis, M. luteus: Micrococcus luteus, S. haemolyticus: Staphylococcus haemolyticus, C. freundii: Citrobacter freundii.*

Figure 6:
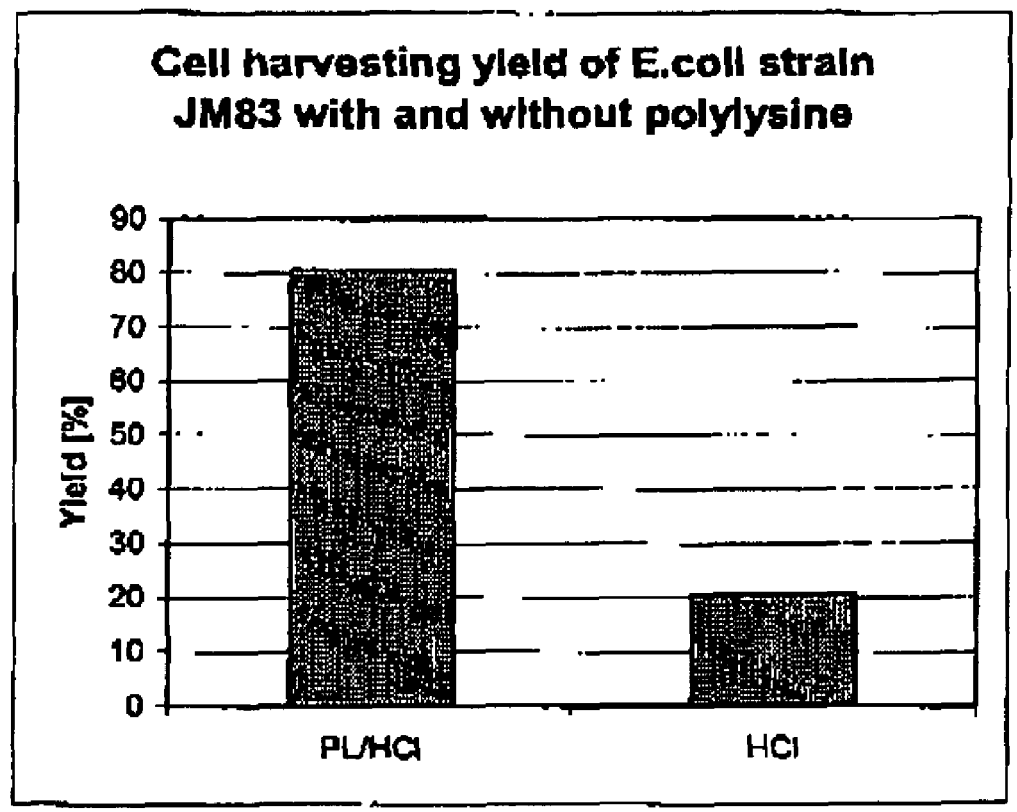

FIG. 6 shows graphically the result of the yield of the cell harvest of the *E. coli* strain JM83 using polylysine in 0.5 M HCl and 0.5 M HCl without polylysine respectively. The values indicate the yield in % determined from the ratio of the optical density of the supernatant and the used cell suspension. PL/HCl: polylysine in 0.5 M HCl; HCl: only 0.5 M HCl (control without polylysine).

Figure 7:
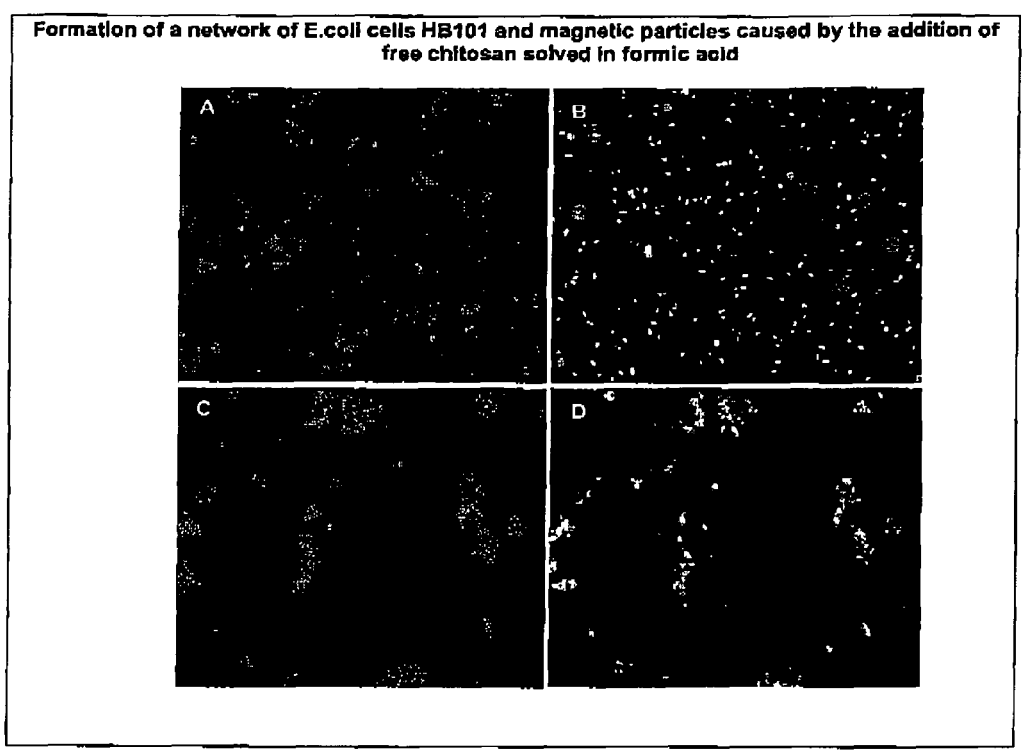

FIG. 7 shows the network-formation of *E. coli* cells, chitosan and magnetic beads. The formation of this net is caused by the administration of free chitosan, solved in 0.5 M formic acid, to an *E. coli* suspension (strain HB 101) (C and D). In the control without chitosan (only 0.5 M formic acid) no network is generated (A and B). The bacteria are represented still as single cells. A and C: Bright field pictures, in A single cells and magnetic pigments and in C aggregates are visible. B and D: fluorescent images after staining of the *E. coli* cells with Propidiumiodide/Syto9 (BacLight™ Viability Kit, Molecular Probes, Eugene, Oreg., USA). In B fluorescent single cells are visible; D shows the fluorescence of the cells which are embedded in the net structures.

Figure 8:
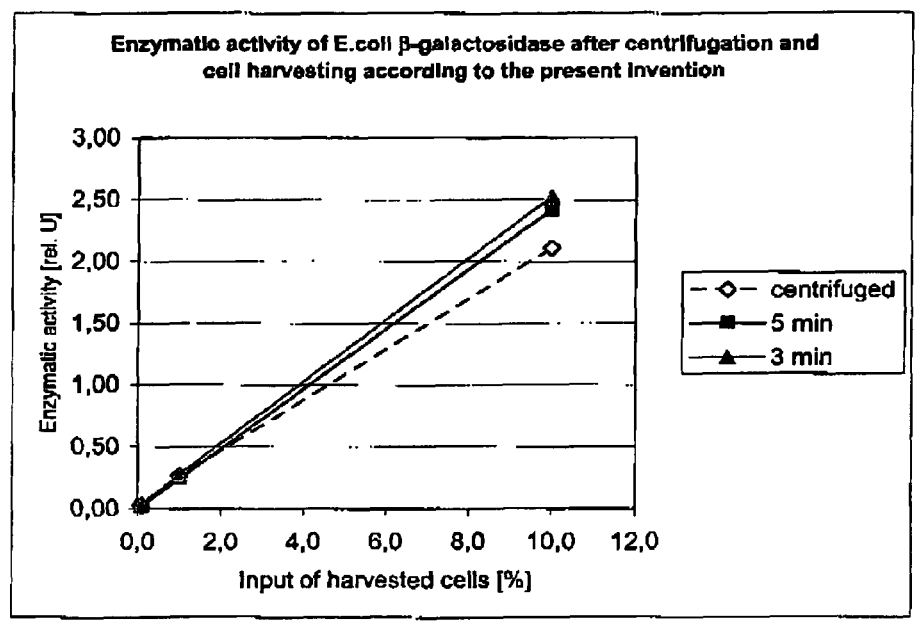

FIG. 8 shows graphically the enzymatic activity of the β-galactosidase of *E. coli* after the cell harvest according to the present invention and after the harvest by centrifugation respectively. The values for the enzymatic activity are plotted in relative units against the fraction of the cells which has been used for the assay consisting of 300 µl of harvested cells (in %). Open diamonds depict values for the centrifuged cells. Triangles and squares depict the values for bacteria that were harvested by the method according to the present invention. Triangles: after addition of 30 µl 125 µg/ml chitosan in 0.5 M formic acid, the cells were incubated for 3 minutes and were separated for further 3 minutes by a magnetic separation procedure. Squares: the bacteria were incubated for 5 minutes and separated in a magnetic field for further 5 minutes after the addition of the solution.

Figure 9:
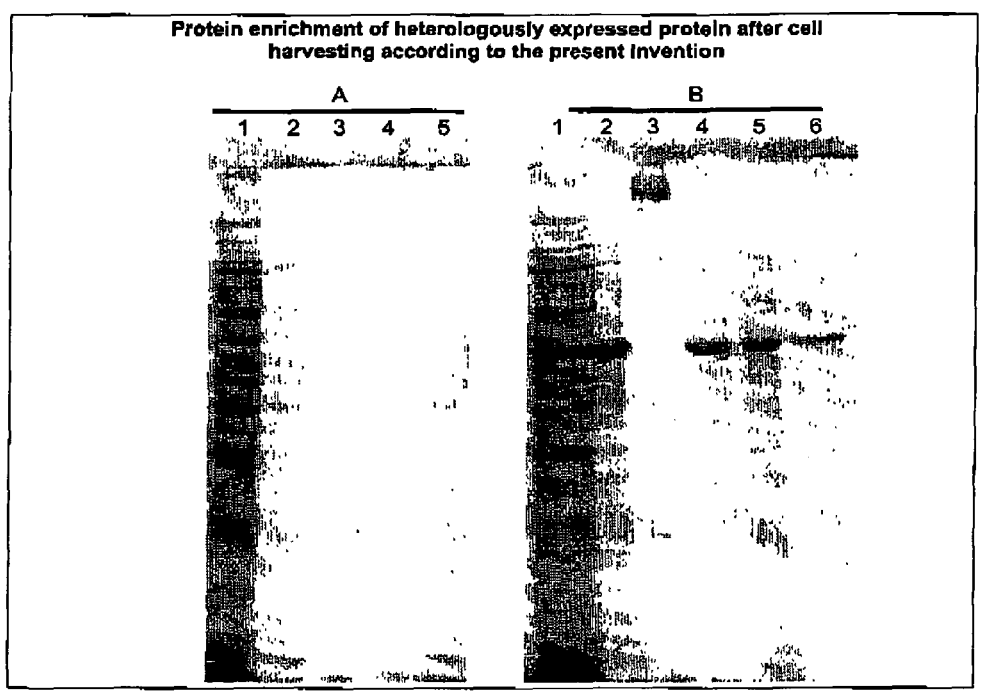

FIG. 9 shows the result of the enrichment of the N-Strep-T4-p12 protein by Strep-Tactin-beads (IBA GmbH, Göttingen, Germany) after the harvest of the heterologously expressing *E. coli* strains BL21(DE3) by the method according to the present invention. A: non induced cells. B: induced cells; 1: crude lysate, 2: strep-tactin-beads after binding of the N-Strep-T4-p12; 3: eluted N-Strep-T4-p12 protein in native, trimeric form; 4: eluted N-Strep-T4-p12 protein in monomeric form (after boiling at 95° C.); 5: strep-tactin-beads after elution; 6: standard (purified N-Strep-T4-p12 protein).

Figure 10:
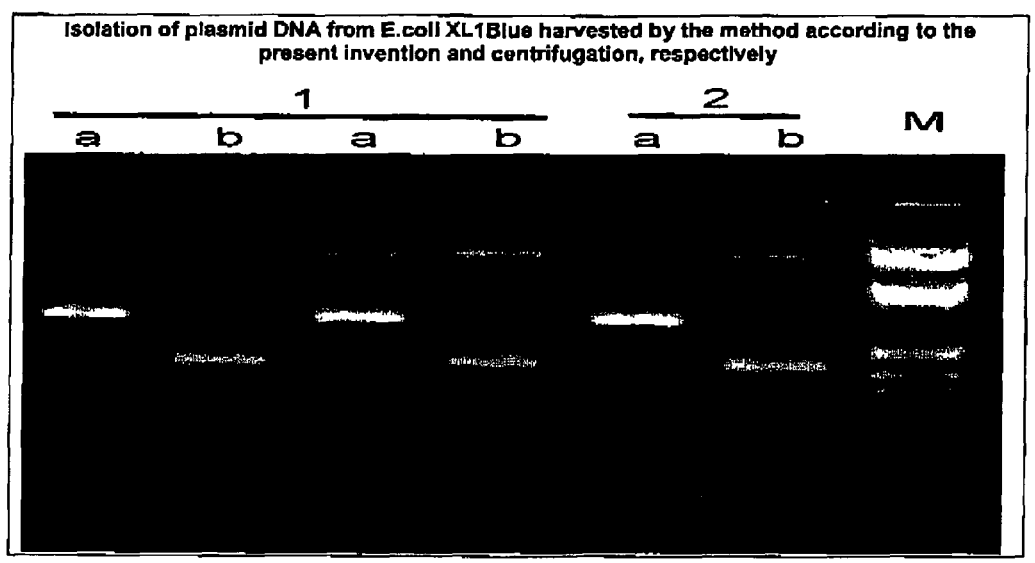

FIG. 10 shows the result of the isolation of the plasmid-DNA from *E. coli* XL1Blue, harvested by the method according to the present invention (as depicted in example 4). 1: harvest of the bacteria by the method according to the present invention; 2: harvest of the bacteria by centrifugation; a: plasmid pUC19 digested with PstI; b: undigested plasmid; M: DNA-standard (Lambda-DNA EcoRI/HindIII).

The herein used term "purification" or "enrichment" denotes the separation of bacterial cells or components of cells from an aqueous solution, e.g. the culture medium in which the bacterial cells or components of cells are located. The purification or enrichment is thereby performed by the use of magnetic particles.

The herein used term "unspecific enrichment" denotes that the enrichment under the conditions chosen is performed independently of the species, strain, genus etc. of the bacteria.

One aspect of the present invention concerns the provision of a method for the unspecific purification of bacterial cells, comprising the following steps:

a) Contacting a sample containing bacterial cells with cationic polymers at an acidic pH-value or anionic polymers at a basic pH-value, b) addition of a magnetic carrier, c) separation of said magnetic carrier with the thereon bound bacterial cells from the sample.

In detail the method is characterised by the following steps:

The bacterial culture is mixed with cationic or anionic polymers in particular with unbranched cationic polymers, preferably with chitosan (e.g. FLUKA Prod. No. 22741, 22742 or 22743, Sigma C-3646 or Roth 5375.1), or polylysine (e.g. Sigma P2636). Preferred anionic polymers are dextransulfate, chondroitinsulfate, polyglutamate, polymalate, polygalacturonic acid, polyphosphate and sulfated oligosaccharides.

The mixture between the bacterial culture and the polymers has to have a certain pH-value according to the used polymers in combination with the respective buffers. The pH-value is preferably lower than or equal to 3 or 4 in the case of cationic polymers, and preferably higher than or equal to 8 in the case of anionic polymers. The pH-value can be adjusted to the desired pH-value either prior to the addition of the polymers by adjusting the bacterial culture by the means of the addition of buffering solutions or directly by the addition of acid or base. In addition the pH-value can be adjusted by solving the polymers in a respective buffer solution or directly in an acid or a base. Moreover the pH-value can be adjusted by adjusting the mixture of bacterial culture and polymer by addition of buffer solutions or directly of acid or a base to the desired pH-value after the addition of polymers. The cationic polymers can be solved in an acidic buffer or directly in an acid. The solution is adjusted such way that the mixture of bacterial culture and cationic polymers results in the desired pH-value, according to the method. For the method according to the present invention, an acidic pH-value of the mixture of the bacterial culture and the polymer is preferred. The pH-value can be adjusted by any buffers or acids, preferably with 0.5 M HCl/25% acetic acid, 0.5 M HCl or 0.5 M formic acid. Which buffer is used, is in particular dependent on the mode of further processing the bacteria and the following method, respectively. If the method according to the present invention shall be used for the purification of plasmids, the buffer HCl/HAc is preferred at a pH-value in the range of about 2 to about 3 because the DNA is hydrolysed at a pH-value lower than 1.8. If the method according to the present invention shall be used for the purification of proteins, formic acid at a pH-value in the range of about 4 is preferred as the buffer because for the isolation of functional proteins the pH-value should be in the range of about 4 to about 9.

The cationic polymers are present in a range of concentration in which a sufficient purification of the bacteria is ensured. Polylysine is used for the precipitation with a concentration in the range of 12.5 µg/ml culture to 150 µg/ml culture, preferentially with the concentration in the range of 25 µg/ml to 150 µg/ml, in particular with a concentration in the range of 40 µg/ml to 75 µg/ml, even more preferred with a concentration of 50 µg/ml. The optimal concentration is thereby dependent on the bacterial species and the bacterial strain respectively, but also on the source of supply or the molecular weight of the polylysine used.

Chitosan is used for precipitation with a concentration in the range of 0.05 µg/ml culture to 100 µg/ml culture, preferentially with a concentration in the range of 0.25 µg/ml to 50 µg/ml, in particular with a concentration in the range of 0.5 µg/ml to 50 µg/ml, moreover in particular with a concentration in the range of 1 µg/ml to 50 µg/ml, even more preferred with a concentration of 2.5-50 µg/ml. Further preferred concentrations which may be dependent on the buffer used arise from the following table. The optimal concentration is thereby dependent on the bacterial species and the bacterial strain respectively, but also on the source of supply or the molecular weight of the chitosan used and the grade of deacetylation of the chitosan. An overview over the preferred concentrations of chitosan can be found in the following table.

| chitosan concentration | chitosan LMW (FLUKA, Prod. No. 22741) | chitosan MMW (FLUKA, Prod. No. 22742) | chitosan HMW (FLUKA, Prod. No. 22743) |
|---|---|---|---|
| HCl/HAc range of concentration for the precipitation | 0.05 µg/ml to 10 µg/ml | 0.05 µg/ml to 5 µg/ml | 1 µg/ml to 20 µg/ml |
| optimal range | 0.5 µg/ml to 5 µg/ml | 0.5 µg/ml to 5 µg/ml | 1 µg/ml to 5 µg/ml |
| optimum | 2.5 µg/ml | | 2.5 µg/ml |
| formic acid range of concentration for the precipitation | 0.5 µg/ml to 50 µg/ml | 0.5 µg/ml to 50 µg/ml | 1 µg/ml to 100 µg/ml |
| optimal range | 0.5 µg/ml to 50 µg/ml | 0.5 µg/ml to 50 µg/ml | 1 µg/ml to 50 µg/ml |
| optimum | 12.5 µg/ml to 50 µg/ml | 12.5 µg/ml to 50 µg/ml | 12.5 µg/ml to 50 µg/ml |

After the addition of the polymers the solution of the bacterial culture and the polymers should be mixed preferably by pipetting up and down or by shaking. By mixing all components involved are brought in contact with each other faster and directly.

The acidified or basic mixture of polymer and bacteria can be processed immediately. However the mixture can also be incubated for a short period of time, preferably for 3-10 minutes, particularly preferred for 5 minutes. The temperature of incubation can be room temperature to 40° C., preferred are 37° C., particularly preferred is room temperature.

The acidified or basic mixture of polymer and bacteria is spiked with a magnetic carrier. Preferably the magnetic carriers are magnetic particles (in the following also called magnetic bead), e.g. polystyrene-beads or magnetic pigments. In the scope of the method according to the present invention polystyrene-beads can be used whose surfaces have been chemically functionalised, especially with $NH_2-$, COOH— or OH-surfaces, wherein the $NH_2$-surface is preferred. As functionalised particles preferably commercially available beads are used e.g. amino-beads (EM2 100/40, diameter 1.43 µm) or carboxy-beads (EM1 100/40, (23710) diameter 1.3 µm) of the company Estapor. As magnetic pigments commercially available beads can be used, e.g. by Bayferrox™ 318M (synthetic iron oxide alpha-$Fe_3O_4$, black pigment), Bayoxid™ E 8706 or Bayoxid™ E8713H (synthetic iron oxides $Fe_3O_4$, technical oxides; Bayer AG). The preferred diameter of the beads resides in the range of 0.5 µm to 2 µm, preferred is the diameter in the range of 1 µm to 5 µm, particularly preferred is about 1 µm.

The method according to the present invention comprises the formation of a network of bacteria and polymers in which magnetic particles of whatever kind, e.g. polystyrene-beads or pigments, are incorporated. Thereby the bacteria can be separated by the magnetic particles which are present in the net by application of a magnetic field.

The method according to the present invention is thereby not restricted to a specific type of magnetic particle which is surface-functionalised but any kind of magnetic particles, which means e.g. a bead or a pigment with various surfaces, can be used. An overview of common kinds of magnets with different surfaces is compiled in the tables A and B. If in the method, according to the present invention, magnetic pigments are used, these pigments can be solved both in alcohol but also in aqueous buffers.

Table A tabularly depicts all magnetic particles which have been tested by now and are functional in the method according to the present invention. Table A: magnetic-pigments indexed by their manufacturers. Table B: magnetic-beads of different basic matrices with different functionalised groups indexed by their manufacturers. PS: polystyrene; silica: silica-matrix; PVA: polyvinylalcohol.

A

| | |
|---|---|
| BASF | Carbonyleisenpulver HQ |
| | Pigment 345 |
| Bayer | Bayferrox 318M, synthetic iron oxide $Fe_3O_4$, black pigment |
| | Bayoxide E8706, synthetic iron oxide $Fe_3O_4$, technical oxide |
| | Bayoxide E8713 H, synthetic iron oxide $Fe_3O_4$, technical oxide |
| | Bayoxide E8710 H, synthetic iron oxide $Fe_3O_4$, technical oxide |
| | Bayoxide E8707 H, synthetic iron oxide $Fe_3O_4$, technical oxide |
| | Bayoxide E8706 H, synthetic iron oxide $Fe_3O_4$, technical oxide |
| EPCOS | Ferrite powder N27 |
| MERCK | Iroidin 600 |
| OMIKRON | Eisenhammerschlag powder, black |
| | ferrous oxide black, strong coloured |
| Vogt | ferrite-powder Fi324 |

TABLE B

| | | |
|---|---|---|
| Estapor | $NH_2$ | PS |
| | COOH | PS |
| | hydrophobic | PS |
| | OH | PS |
| Spherotech | $NH_2$ | PS |
| | COOH | PS |
| | hydrophobic | PS |
| Polysciences | BioMag $NH_2$ | PS |
| | BioMagCOOH | PS |
| | PS, paramagnetic | PS |
| | $NH_2$, paramagnetic | PS |
| MERCK | MagPrep Silica | Silica |
| Micromod | Sicastar M-$NH_2$ | Silica |
| | Sicastar M-plain | Silica |
| | Nanomag C, plain | Ferrofluide |
| Chemagen | M-PVA 011, OH | PVA |
| | M-PVA 012, OH | PVA |
| | M-PVA 013, OH | PVA |

The magnetic particles are present in a range of concentration in which a sufficient purification of the bacteria is ensured, but the expenses of the purification are in a justifiable scope. Preferably the polystyrene-beads are added with a 1% polystyrene-bead solution in a concentration of about 1/10 to 1/70 of the volume of the bacterial culture. Particularly preferred is a concentration of about 1/20 to 1/50, in particular a concentration of 1/20 or 1/50. Thereby the concentration is dependent on the size of the volume of the bacterial culture. Is the volume of the bacterial culture e.g. 0.2 or 1 or 1.5 ml a concentration of the 1% polystyrene-bead-solution of 1/20 is preferred, and with a volume of the bacterial culture of e.g. 10 ml a concentration of the 1% polystyrene-bead-solution of 1/50 is preferred. The greater the volume of the bacterial culture is, the lower the concentration of the polystyrene-bead may be. The magnetic pigments are preferably used as a 5%-solution with a concentration of 1/10 volumes of the bacterial culture.

After the addition of the magnetic particles the solution of the bacterial culture, polymer and magnetic particles should be mixed preferably by pipetting up and down, shaking or with a magnetic stirrer. By mixing all involved components are brought into contact with each other faster and directly.

The mixture can be processed immediately. However the mixture can also be incubated for a short period of time, preferably for 3-10 minutes, particularly preferred for 5 minutes. The incubation temperature can be room temperature to 40° C., preferred are 37° C., particularly preferred is room temperature.

Subsequently the bacteria, which are bound to the magnetic carrier, are separated from the sample. Thereby the mixture of bacteria, polymer and magnetic particles is inserted into a magnetic field and the complex is precipitated.

The magnetic particles which have been bound to the bacteria in the preceding steps of the method can be separated from the bacteria, depending on the kind of the further processing—e.g., plasmid-preparation, preparation of RNA or genomic DNA—by shaking and being discarded, or they can be used in the further steps of processing along with the bacteria. If the bacteria are to be separated from the magnetic particles, the mixture of bacteria, polymer and magnetic particles can be resuspended again in the respective buffer after the separation from the sample, and be removed and e.g. transferred into a new reaction tube, simultaneously detaining the magnetic particles by a magnet. For detaching the bacteria from the network of bacteria, polymer and magnetic particles, preferentially a Tris-buffer (200 mM, pH 8-9.5) is used. For detaching preferentially a shaking step is performed at high rotation, e.g., at 1200 rpm (Eppendorf rotary shaker).

The method according to the present invention can be carried out in all common reaction tubes, preferentially in Eppendorf reaction tubes of all kinds or in micro-titre-plates.

The bacteria, which can be enriched by the method according to the present invention, can be all kinds of bacteria preferentially *eubacteria* and *archaebacteria*, especially *E. coli*, in particular BL21, JM109, *E. coli* B, DH1, LE392, *E. coli* K12, DH5α, NM522, *E. coli* C., DH10b, Sure, GM2163, TG2, HB101, Top10, InvaF', XL1Blue, JM83, but also *Micrococcus* spec. in particular *Micrococcus luteus*, *Proteus* spec. in particular *Proteus mirabilis*, *Enterococcus* spec. in particular *Enterococcus faecalis*, *Citrobacter* spec. in particular *Citrobacter freundii*, *Bacillus* spec. in particular *Bacillus vallismortis*, *Staphylococcus* spec. in particular *Staphylococcus haemolyticus*.

The method according to the present invention can be used as an alternative to centrifugation and can therefore facilitate the automatic purification of bacterial cells. With the depicted method bacteria can be unspecifically enriched from a culture within about 5-10 minutes. Since the concentration of the used cationic polymers is very low being under 1%, the enrichment procedures can be performed at considerably lower costs than with procedures according to the state of art. Furthermore in the method according to the present invention considerably less amounts of beads of 1-15 beads per bacterium, instead of 30-50 beads per bacterium, e.g. as described in WO 00/29562, are used.

The following examples serve for elucidation and do not limit the scope of the invention in any respect.

1. Preparation of the Chitosan Solution

Chitosan was weighed, resuspended in 0.5 N HCl/25% HAc and the solution was heated (ca. 80-90° C.) until the chitosan was completely solved. Subsequently the solution was diluted and adjusted to 25 µg/ml in 0.5 N HCl/25% HAc (=working solution H) or to 125 µg/ml in 0.5 N formic acid (=working solution A). The working solution (25 µg/ml) stays stable in solution at room temperature and was stored that way.

2. Preparation of the Polylysine Solution

Polylysine was weighed, resuspended in 0.5 N HCl and adjusted to 0.5 mg/ml in 0.5 N HCl (=working solution). The working solution was stored at −20° C. until use.

3. The Harvest of Bacteria in a Scale of 0.2 ml Culture: Formation of the Network The culture of *E. coli* HB101 was performed overnight in a 0.5 ml 96-well polypropylene-micro-titre-plate with 0.2 ml culture per well. 20 µl chitosan working solution A and 20 µl 0.5 M formic acid respectively without chitosan in the control sample, and 20 µl of a 5% solution of the magnetic pigment Bayoxid™ E8706 (synthetic iron oxide $Fe_3O_4$, technical oxide) in PBS were added to the culture and mixed by pipetting up and down. After an incubation period for 5 minutes at room temperature the samples were microscoped to check the formation of the network (FIG. 7).

4. Harvest of the Bacteria in the Scale of 1.5 ml Culture: DNA-Isolation

The cultivation of *E. coli* XL1Blue transformed with the plasmid pUC19 was performed in a 96-DWP overnight with 1.25 ml culture volume each per well in LB-medium with 100 µg/ml ampicillin. 125 µl chitosan working solution H and 125 µl of a 5% pigment bead solution (Bayferrox™ 318M, synthetic iron oxides $Fe_3O_4$, black pigment, in isopropanol) were added to the overnight culture and mixed well by pipetting up and down. After an incubation period of 5 minutes at room temperature the bacteria/beads complexes were separated on a magnetic separator (Bilatec AG, Mannheim, Germany). The supernatant was removed completely and the plasmid DNA was isolated from the cell sediment, using the DNA-isolation-kit Wizard MagneSil™ plasmid purification system (kit using alkaline SDS-lysis to generate the bacterial lysate and incorporating silica Paramagnetic Particles for both lysate clearing and plasmid purification; Promega, Madison, USA), according to the manufacturers protocol (FIG. 10).

5. Harvest of the Bacteria in the Scale of a 10 ml Culture

The cultivation of *E. coli* JM83 was performed in a polypropylene-tube overnight with 10 ml culture volume. 1 ml (1/10 volume) chitosan working solution H was added to the overnight culture and mixed by pipetting up and down twice. After this 0.2 ml of a 1% amino-polystyrene-bead-solution was added. Subsequently the solution was mixed by pipetting up and down (twice). Afterwards an incubation at room temperature for 5 minutes followed. The tube was inserted into a magnetic field of a permanent magnet (Bilatec AG, Mannheim, Germany) for 10 minutes in order to sediment the bacteria/bead-complexes. The supernatant was discarded and the bacterial cells were processed directly.

6. Cultivation of the *E. Coli* Cultures

*E. coli* cultures were cultivated overnight in standard media, like LB, 2×YT, SOB or SOC (Maniatis, 1987). 200 µl of the overnight cultures were each spiked with 20 µl chitosan working solution H and 20 µl amino-polystyrene-beads and mixed well. After 5 minutes of incubation the separation of the bacteria beads-complexes was performed on a magnetic separator. If the mentioned media are used, an adjustment of the concentrations of the working solution and the beads might be necessary.

7. Harvest of the Bacteria in the Scale of a 0.2 ml Culture

The cultivation of 0.2 ml cultures of *Enterococcus faecalis, Proteus mirabilis, Staphylococcus haemolyticus* was performed in a 96-microwell-plate overnight at 37° C. The cultivation of 0.2 ml cultures of *Bacillus vallismortis, Micrococcus luteus, Citrobacter freundii* was performed in a 96-microwell-plate overnight at 30° C. 20 µl (1/10 volume) chitosan working solution H were added to the overnight culture. After this 10 µl of a 1% amino-polystyrene-bead-solution were added. Subsequently the solution was mixed in the well by pipetting up and down (1 or 2 times). An incubation at room temperature for 5 minutes followed. The micro-titre-plate was incubated for 5 minutes on a magnetic separator (Bilatec AG, Mannheim, Germany) for sedimentation of the bacteria/bead-complexes. The supernatant was discarded and the bacterial cells were processed directly.

8. Harvest of Living Bacteria

30 µl chitosan working solution A and 30 µl of a 5% pigment bead-solution (Bayferrox™ 318M; synthetic iron oxides $Fe_3O_4$, black pigment; in PBS) were added to 300 µl of an overnight culture of *E. coli* BL21 (DE3) in a 0.5 ml 96-well PP-micro-titre-plate and mixed well by pipetting up and down. After this an incubation step was performed for 3 and 5 minutes respectively at room temperature. Subsequently the bacteria/bead-complexes were sedimented by incubation on a suitable magnetic separator (Bilatec AG, Mannheim, Germany) for 3 and 5 minutes respectively. The supernatant was discarded and the bacteria/bead-pellets were each resuspended in 200 µl of 200 mM Tris pH 8.0. For a control 300 µl of an overnight culture were centrifuged and the pellet was also resuspended in 200 µl of 200 mM Tris pH 8.0. The vitality of the cells was checked by plating dilution series on agar-plates and the colonies were counted after an overnight incubation. As a further assay for the activity and the viability of the cells, the enzymatic activity of the cell's own β-galactosidase (Apte et al., 1995, Wat. Res. 29, 1803-1806) was measured (FIG. 8).

9. Protein Isolation:

For the protein isolation from bacteria that have been harvested by the method according to the present invention, the Strep-tag-system was used. Therefore p12 (Selivanov, N. A., et al., 1988, Nucleotide and deduced amino acid sequence of bacteriophage T4 gene 12, Nucleic Acids Rs.; 16(5): 2334) was fused to an N-terminal Strep-tag (U.S. Pat. No. 5,506,121), using molecular biological standard methods and expressed as described by Burda, M. R. & Miller S. (Europ. J. Biochem, 1999, 265: 771-778). The cultivation of the N-Strep-T4-p12 expressing *E. coli* strain BL21(DE3) pNS-T4-p12p57 was performed in a 96-deepwell-plate with 1.25 ml culture per well. At a cell density $OD_{600}$ of about 0.5 the induction took place with 1 mM IPTG for 3 h. Subsequently 125 µl chitosan working solution A and 125 µl of a 5% pigment-bead solution (Bayoxid E8706 in PBS) were added per well, mixed well by pipetting up and down and incubated at room temperature for 5 minutes.

After this the bacteria/bead-complexes were sedimented by an incubation on a suitable magnetic separator (Bilatec AG, Mannheim, Germany) for 5 minutes. The supernatant was removed completely and the pellet was resuspended in 150 µl buffer A (200 mM Tris pH 8.0, 200 mM NaCl, 10 mM EDTA, 0.05% Tween20). Subsequently the bacteria were detached from the bacteria/bead-net by a shaking step (of 5 minutes at 1200 rpm, shaker of the company Eppendorf, Germany). The beads were separated from the cells, being now present in the supernatant, by a repeated incubation on the magnetic separator and the supernatant was transferred to a new well of a 0.5 ml 96-well PP-micro-titre-plate. The cells were subsequently lysed by the addition of lysozyme (1.6 mg/ml), a shaking period of 2 minutes at 750 rpm and an incubation for 15 minutes at room temperature, and the DNA was digested by the addition of 5 µg/ml DNAse. The heterologously expressed N-Strep-T4-p12 was bound to the StrepTactin-beads by the addition of 10 µl of 5%-StrepTactin-beads (Company IBA, Göttingen, Germany) and an incubation at smooth shaking for 20 minutes and enriched from the lysate. The N-Strep-T4-p12 was eluted from the beads by adding 5 mM biotin (FIG. 9).

The invention claimed is:

1. A method for separating bacteria from a sample comprising:
   a) preparing a mixture comprising the bacteria-containing sample and a cationic polymer at an acidic pH and in the absence of magnetic particles, whereby a polymer network comprising the bacteria is formed;
   b) adding to the mixture a magnetic carrier comprising a magnetic pigment or a magnetic polystyrene-bead; and
   c) separating the polymer network comprising the magnetic carrier and the bacterial cells embedded in the polymer network by precipitation from the mixture.

2. The method of claim 1, wherein the cationic polymer is chitosan or polylysine.

3. The method of claim 2, wherein cationic polymer is chitosan, whose concentration is from 0.05 to 100 µg/ml culture.

4. The method of claim 2, wherein the cationic polymer is polylysine, whose concentration is from 12.5 to 150 µg/ml culture.

5. The method of claim 1, wherein the magnetic carrier is a magnetic pigment or a magnetic polystyrene-bead with a $NH_2$—, COOH— or OH-surface.

6. The method of claim 1, wherein the sample is incubated with the cationic polymer at room temperature.

7. The method of claim 1, wherein the pH is at or below 4.

8. The method of claim 1, wherein the pH is at or below 3.

9. The method of claim 1, wherein the bacteria are gram-positive.

10. The method of claim 1, wherein the bacteria are gram-negative.

11. The method of claim 1, further comprising separating the bacteria from the polymer network following step c).

12. A method for separating bacteria from a sample comprising:
   a) preparing a mixture comprising the bacteria-containing sample and chitosan or polylysine at a pH at or below 4 and in the absence of magnetic particles, whereby a polymer network comprising the bacteria is formed;
   b) adding to the mixture a magnetic pigment or a magnetic polystyrene-bead; and
   c) separating the polymer network comprising the magnetic pigment or a magnetic polystyrene-bead and the bacteria by precipitation from the mixture.

13. The method of claim 12, further comprising separating the bacteria from the polymer network following step c).

* * * * *

UNITED STATES PATENT AND TRADEMARK OFFICE
CERTIFICATE OF CORRECTION

PATENT NO. : 7,868,144 B2  
APPLICATION NO. : 10/492230  
DATED : January 11, 2011  
INVENTOR(S) : Sabine Diller Page 1 of 1

It is certified that error appears in the above-identified patent and that said Letters Patent is hereby corrected as shown below:

In title page, item (56) References Cited - FOREIGN PATENT DOCUMENTS, insert
--DE 19520398    12/12/96
  DE 4307262     09/08/94
  WO 00/29562    05/25/00
  WO 92/07863    05/14/92--

Signed and Sealed this  
Fifth Day of July, 2011

David J. Kappos  
*Director of the United States Patent and Trademark Office*